United States Patent
Tucker et al.

(10) Patent No.: US 12,131,814 B2
(45) Date of Patent: Oct. 29, 2024

(54) REAL-TIME FEEDBACK MODULE FOR ASSISTIVE GAIT TRAINING, IMPROVED PROPRIOCEPTION, AND FALL PREVENTION

(71) Applicant: California Institute of Technology, Pasadena, CA (US)

(72) Inventors: Maegan Tucker, Pasadena, CA (US); Aaron D. Ames, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 957 days.

(21) Appl. No.: 16/938,654

(22) Filed: Jul. 24, 2020

(65) Prior Publication Data

US 2021/0027877 A1     Jan. 28, 2021

Related U.S. Application Data

(60) Provisional application No. 62/878,037, filed on Jul. 24, 2019.

(51) Int. Cl.
*G16H 20/30* (2018.01)
*A61H 3/02* (2006.01)
*G06F 3/01* (2006.01)

(52) U.S. Cl.
CPC ............. *G16H 20/30* (2018.01); *A61H 3/02* (2013.01); *G06F 3/016* (2013.01); *A61H 2201/0173* (2013.01); *A61H 2201/1207* (2013.01); *A61H 2201/1621* (2013.01); *A61H 2201/165* (2013.01); *A61H 2201/501* (2013.01); *A61H 2201/503* (2013.01); *A61H 2201/5038* (2013.01); *A61H 2201/5046* (2013.01); *A61H 2201/5097* (2013.01); *A61H 2203/04* (2013.01)

(58) Field of Classification Search
CPC .......... G16H 20/30; G16H 40/63; A61H 3/02; A61H 2201/0173; A61H 2201/1207; A61H 2201/1621; A61H 2201/165; A61H 2201/501; A61H 2201/503; A61H 2201/5038; A61H 2201/5046; A61H 2201/5097; A61H 2203/04; A61H 2201/0165; A61H 3/061; A61H 2201/1635; A61H 2201/5012; A61H 2201/5064; A61H 2201/5069; A61H 2201/5084; G06F 3/016
USPC ...................................... 340/573.1
See application file for complete search history.

(56) References Cited

U.S. PATENT DOCUMENTS

| | | | |
|---|---|---|---|
| 7,892,147 B2 * | 2/2011 | Vick, Jr. ............ | A63B 23/0244 482/142 |
| 9,878,751 B1 * | 1/2018 | Thorne ................ | B62D 57/032 |
| 10,113,877 B1 * | 10/2018 | Schaefer ............ | G01C 21/3629 |
| 10,182,746 B1 * | 1/2019 | Demiralp .............. | G06F 18/213 |
| 10,481,688 B1 * | 11/2019 | Wang ...................... | G06F 3/014 |

(Continued)

OTHER PUBLICATIONS

Burns, E.R., et al., "The direct costs of fatal and non-fatal falls among older adults—United States", Journal of Safety Research, Sep. 2016, pp. 99-103, vol. 58.

*Primary Examiner* — Omar Casillashernandez
(74) *Attorney, Agent, or Firm* — Gates & Cooper LLP

(57) ABSTRACT

A device providing real-time feedback to users to aid in gait training or other applications where awareness of body position is useful. Embodiments of the device equip patients to regain balance and practice physical therapy exercises in either a clinical setting or at home.

18 Claims, 18 Drawing Sheets

(56) References Cited

U.S. PATENT DOCUMENTS

| | | | | |
|---|---|---|---|---|
| 11,640,767 | B1* | 5/2023 | Bridges | G09B 5/02 |
| | | | | 434/257 |
| 2010/0172529 | A1* | 7/2010 | Burns | H04R 25/50 |
| | | | | 381/328 |
| 2011/0313327 | A1* | 12/2011 | Van Acht | A61B 5/4528 |
| | | | | 600/595 |
| 2012/0191016 | A1* | 7/2012 | Jastram | A61B 5/1117 |
| | | | | 600/595 |
| 2016/0331557 | A1* | 11/2016 | Tong | A61F 2/6607 |
| 2017/0086785 | A1* | 3/2017 | Bjaerum | A61B 8/4444 |
| 2017/0128816 | A1* | 5/2017 | DeMarch | G09B 19/003 |
| 2017/0224573 | A1* | 8/2017 | Challa | A45B 9/04 |
| 2018/0317813 | A1* | 11/2018 | Hall | A61B 5/7435 |
| 2019/0132948 | A1* | 5/2019 | Longinotti-Buitoni | |
| | | | | A61B 5/743 |
| 2019/0192053 | A1* | 6/2019 | Saigh | G16H 20/30 |
| 2020/0258365 | A1* | 8/2020 | Ten Kate | G08B 21/0446 |
| 2020/0368099 | A1* | 11/2020 | Crosby | A61H 1/00 |
| 2020/0391080 | A1* | 12/2020 | Powers | G16H 50/50 |
| 2021/0027877 | A1* | 1/2021 | Tucker | G16H 40/63 |
| 2021/0186376 | A1* | 6/2021 | Becker | A61B 5/7455 |
| 2021/0379774 | A1* | 12/2021 | Pounds | B62D 57/032 |
| 2022/0257968 | A1* | 8/2022 | Wu | A46B 15/00 |
| 2023/0146673 | A1* | 5/2023 | Augarten | A61B 1/0684 |
| | | | | 600/180 |
| 2023/0201694 | A1* | 6/2023 | Yoo | A63B 21/063 |
| | | | | 482/8 |

* cited by examiner

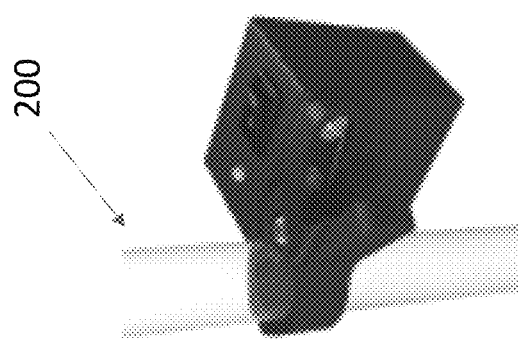
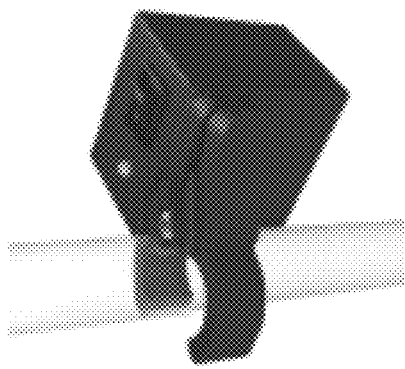
Figure 3

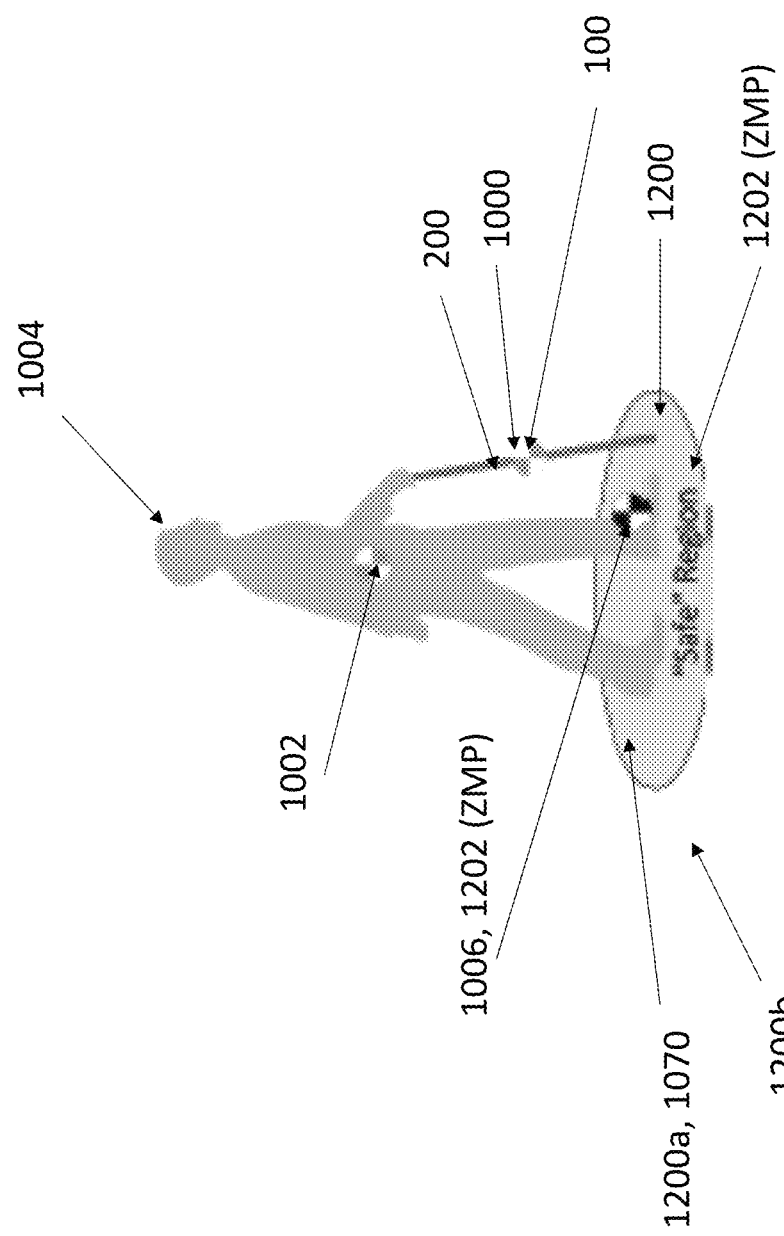

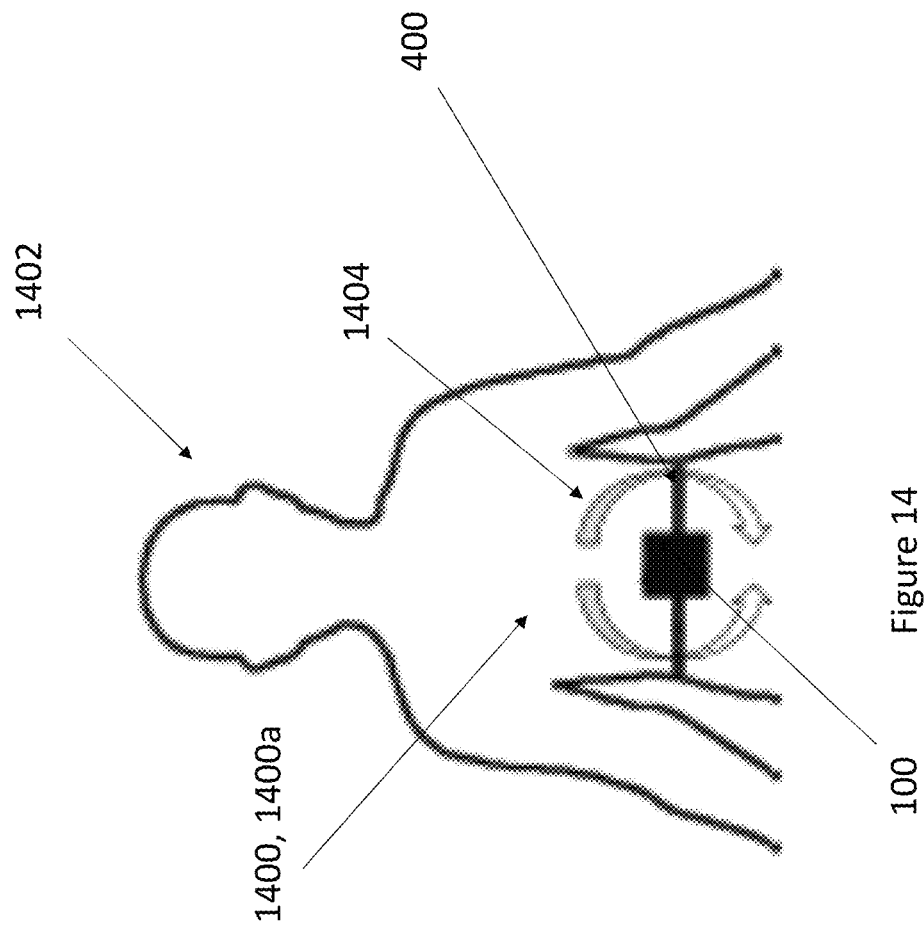

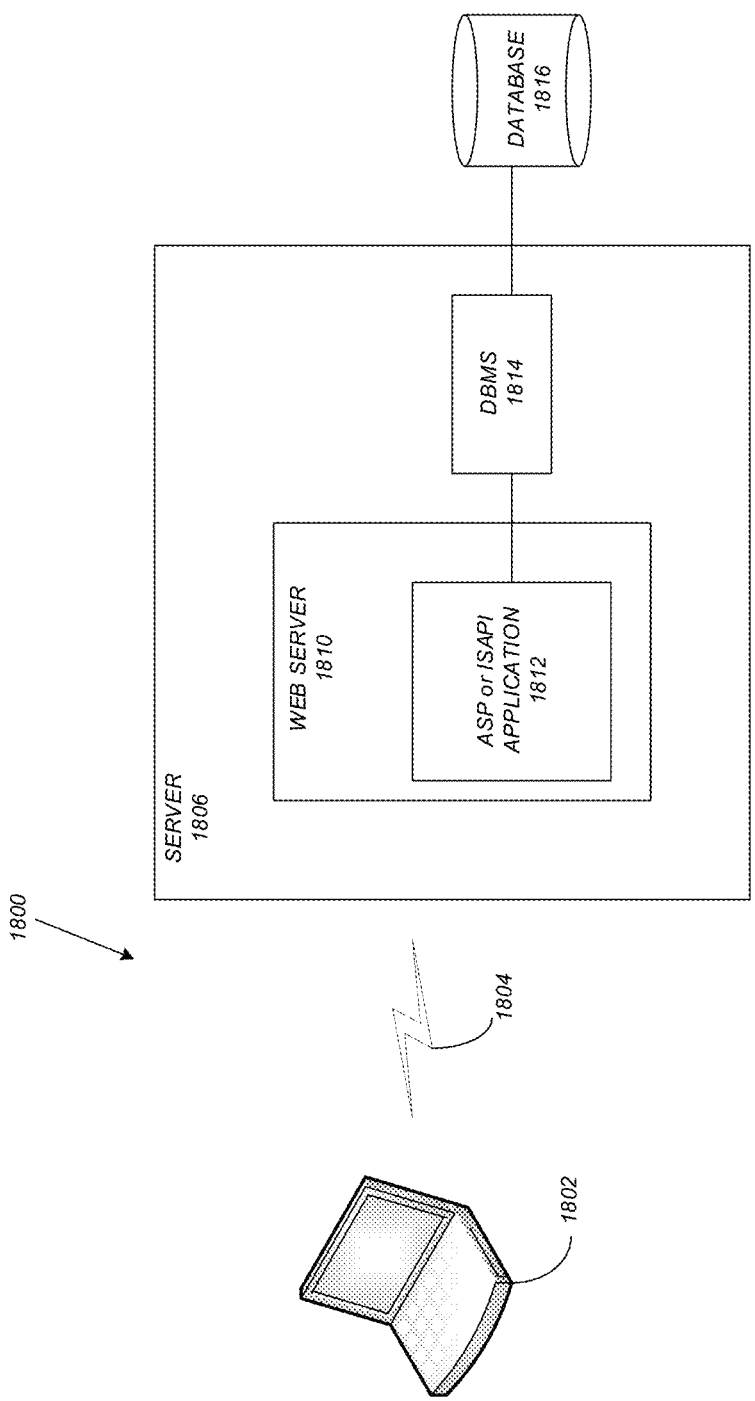

REAL-TIME FEEDBACK MODULE FOR ASSISTIVE GAIT TRAINING, IMPROVED PROPRIOCEPTION, AND FALL PREVENTION

CROSS REFERENCE TO RELATED APPLICATIONS

This application claims the benefit under 35 USC 119(e) of commonly assigned U.S. Provisional Patent Application Ser. No. 62/878,037, filed Jul. 24, 2019, by Maegan Tucker, entitled "Real-Time Feedback Module For Assistive Gait Training, Improved Proprioception, And Fall Prevention," which application is incorporated by reference herein.

BACKGROUND OF THE INVENTION

1. Field of the Invention

The present disclosure relates to systems and methods for gait training, rehabilitation, or posture correction.

2. Description of the Related Art

Falls are a prevalent and expansive problem that must be addressed in present-day society. In 2015, falls cost Medicare over $31 billion [1]. Moreover, according to the U.S. Centers for Disease Control and Prevention, over 800,000 patients a year are hospitalized because of a fall injuries.

The possible solutions for fall prevention can be split up into two main categories: walking aids and training. Training includes both physical therapy and strength training. Some physical therapists encourage the elderly to strengthen their core, which is a key part of balancing and walking without falling. According to American Physical Therapy Association (APTA), patients can improve walking ability and balance through various coordination activities such as obstacle courses, dancing, or Tai Chi. However, APTA also states that for some individuals, there are multiple issues that might affect balance and that these patients require a combination of different types of interventions with therapy. Although therapy helps to increase independence, gerontology experts recommend that individuals do these exercises daily and even then, the positive effect is not immediate and cannot prevent all types of falls. Additionally, it is infeasible for most of the elderly population to either afford the treatments or remember to do them daily. For this reason, it is important that individuals with low mobility also use a walking aid to prevent falls.

The primary types of walking aids include canes, walkers, and crutches. Currently, according to the National Institutes of Health, approximately 6.5 million people use a cane, walker, or crutches to assist with mobility. Some of the major benefits of canes are versatility, lightness, and low cost. Additionally, they are customizable and portable. However, in some cases, canes are not an effective solution. This is primarily the case if a user does not have strength in their limbs or if users are unaware that they are using the cane incorrectly and in an unsafe manner. Overall, canes are a very valuable tool used to help individuals regain mobility. However, even with the use of a cane, it is imperative that patients practice either balance exercises or work with physical therapists to regain balance to effectively prevent falls.

Nearly all commercial canes currently on the market are passive devices. The only, exception are canes that have an LED light at the bottom. Existing technology-enhanced canes focus on built in technology to record the bio-mechanic behavior of the user and report it to a clinician. Clinicians can then use this data to correct the walking gait of the user. What is needed, then, are technology assisted aids that more effectively and rapidly communicate with a user. Embodiments described herein satisfy this need.

SUMMARY OF THE INVENTION

The present disclosure describes an apparatus useful for performing therapy or other corrective measures. The apparatus can be embodied in many ways including, but not limited to, the following.

1. An apparatus, comprising:
 a sensor measuring a measurement of at least one parameter associated with a position of a body part of a user or equipment attached to the user; and
 a sensory output device outputting a feedback to the user based on the measurement received from the sensor and in real time with the measuring, the feedback communicating to the user whether the position is acceptable or unacceptable for maintaining balance, correct posture, or following a predetermined physical therapy or rehabilitation exercise.

2. The apparatus of example 1, wherein the feedback is provided to the user within 100 milliseconds of the sensor measuring the measurement.

3. The apparatus of example 1 or 2, wherein the device is a haptic device and the feedback comprises a haptic feedback felt by the user.

4. The apparatus of any of the preceding examples, wherein the sensor comprises an inertial measurement unit (IMU). Example devices include at least one of a multi axis accelerometer, gyroscope, or other sensors to provide estimation of an object's orientation in space. Measurements of acceleration, angular rate, and attitude are typical data outputs. In one or more examples, the accelerometer is a 6 axis accelerometer, a 9 axis accelerometer, or an accelerometer having 6 axes or less. Examples include, but are not limited to, an MPU 6050.

5. The apparatus of any of the preceding examples, wherein the sensory output device comprises a vibration motor.

6. The apparatus of any of the preceding examples, further comprising a computer (e.g., processor) determining whether the at least one parameter is in a predetermined range associated with the acceptable position or the unacceptable position and the feedback communicates to the user when the at least one parameter is within the predetermined range.

7. The apparatus of example 6, wherein the predetermined range is tailored to the user and comprises data representing acceptable positioning of the body part during the physical therapy exercise customized for the user.

8. The apparatus of example 6, further comprising a computer inputting the at least one parameter into a model or algorithm determining whether the at least one parameter lies on an acceptable trajectory commensurate with a predetermined trajectory for the physical therapy exercise or for maintaining the balance or the posture.

9. The apparatus of example 6, further comprising a computer inputting the at least one parameter into a model or algorithm determining whether the at least one parameter is associated with the acceptable or unacceptable position.

10. The apparatus of any of the preceding examples, wherein the position comprises an orientation and the feedback communicates whether the orientation is within or outside an acceptable range so as to guide or train a walking gait of the user.

11. The apparatus of example 10, further comprising a computer determining whether the orientation lies within a predetermined range for stability of the user so as to avoid a fall.

10. The apparatus of example 11, wherein the predetermined range comprises an angle within 20 degrees of an axis passing through a torso of the user or a longitudinal axis of a walking stick or cane attached to the apparatus.

12. The apparatus of example 10 or 11, wherein the stability is defined using a zero-moment point of the user and the computer calculates the zero-point moment of the user in real time using the orientation.

13. A walking stick or cane comprising the apparatus of any of the preceding examples, 14. The walking stick or cane comprising the apparatus of example 13 and a handle, wherein the sensory output device comprises a vibration motor attached to the handle.

15. The apparatus of any of the examples 1-12, further comprising a strap for attaching the apparatus to the body part comprising a torso.

16. The apparatus of any of the preceding examples, wherein the feedback communicates the acceptable position so as to provide positive reinforcement to the user.

17. An article of clothing or wearable article comprising the apparatus of any of the preceding examples.

In one or more examples, the technology is used to help users better understand balance and safely perform rehabilitation exercises such as walking with a cane or standing upright. An example of such a rehabilitative task includes transitioning from a multi-point cane to a single-point cane. In one or more examples, the balance module serves the population of people who are recovering from balance impairment such as strokes. Thus, a target market for this device includes individuals training to regain balance through rehabilitation.

In one or more examples, the device notifies the user of when they perform actions that deviate away from an upright and thus balanced position. In one embodiment placed on a cane, the device provides haptic feedback through vibrations of a vibration motor to notify the user of when the cane is tilted in the direction perpendicular to the direction of walking. The module obtains information about its orientation through the use of an Inertial Measurement Unit. This information is processed by a microprocessor which directly sends signals to the vibration motor. The module is powered using a (e.g., 9V) battery. The module is connected to the cane using a custom clamp. A flat version of the clamp can also be used to attach the module directly to the clothing of a user.

BRIEF DESCRIPTION OF THE DRAWINGS

Referring now to the drawings in which like reference numbers represent corresponding parts throughout:

FIG. 3: Clamp Design
FIG. 12: Representation of Zero-Moment Point (ZMP)
FIGS. 13A and 13B: Active Stabilization Examples, wherein
FIG. 13A illustrates an example module with a flywheel that stabilizes the orientation of the cane about the central axis and FIG. 13B illustrates an example module wherein the flywheel provides active stabilization that directly corrects for angle deviations laterally in the frontal plane.
FIG. 14: Module for Trunk Alignment Corrections.
FIG. 18. Example network environment.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

TECHNICAL DESCRIPTION

I. Example Apparatus

FIGS. 1-6 illustrate various views of an apparatus 100 comprising a sensor 102 measuring a measurement of at least one parameter associated with a position of a body part of a user or equipment attached to the user; and a sensory output device 104 outputting a feedback to the user based on the measurement received from the sensor and in real time with the measuring. The feedback communicates to the user whether the position is acceptable or unacceptable for maintaining balance, correct posture, or following a predetermined physical therapy or rehabilitation exercise, for example.

Figure 1:
FIG. 1: Front View of Module
Figure 2:
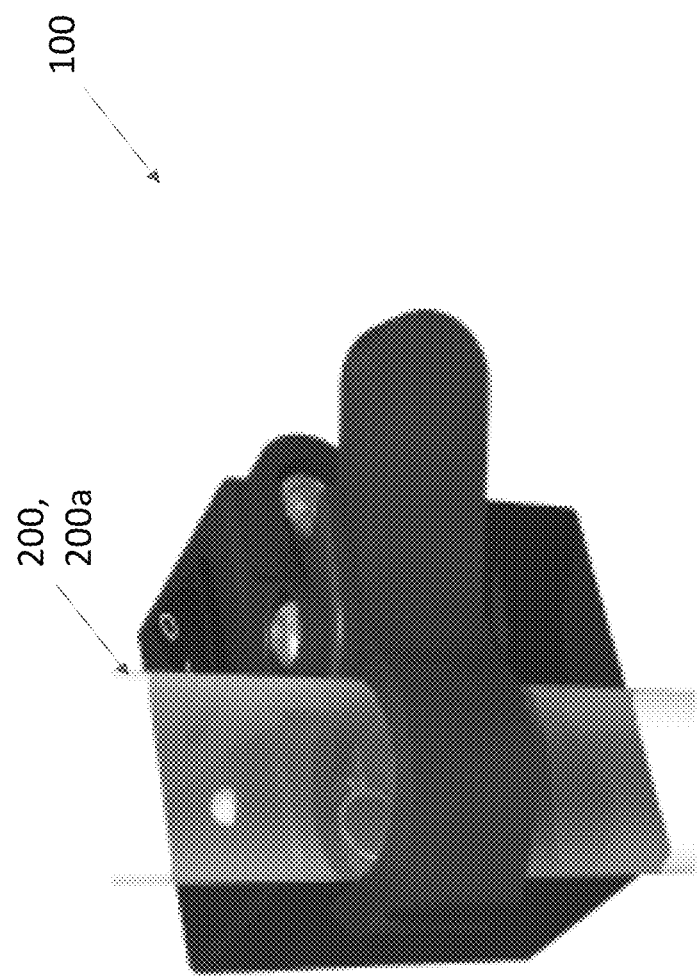
FIG. 2: View of Vibration Motor Attachment
Figure 4:
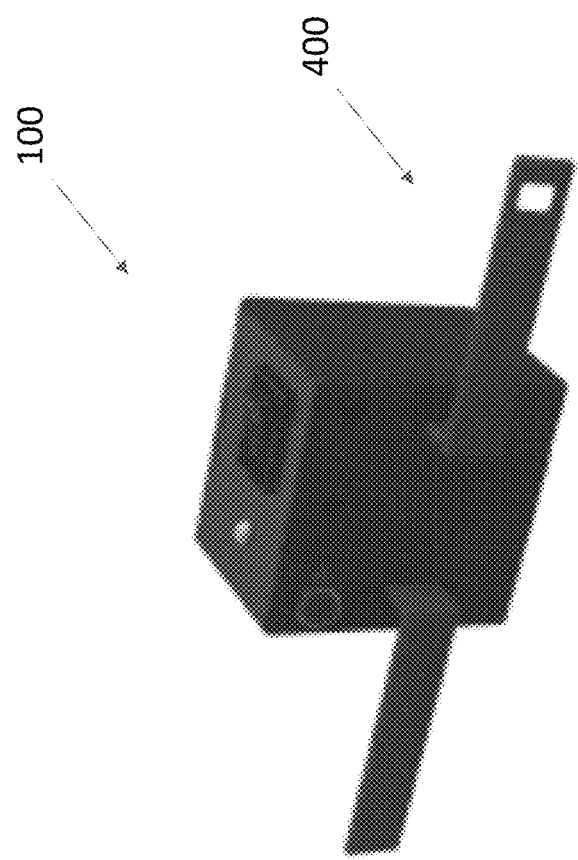
FIG. 4: Module with flexible Straps

FIGS. 1-3 illustrate a walking stick or cane 200 comprising the apparatus 100, wherein the apparatus is attached to the stick or cane using a clamp 202. FIG. 4 illustrates a flexible strap 400 for attaching the apparatus to equipment or a body part.

Figure 5:
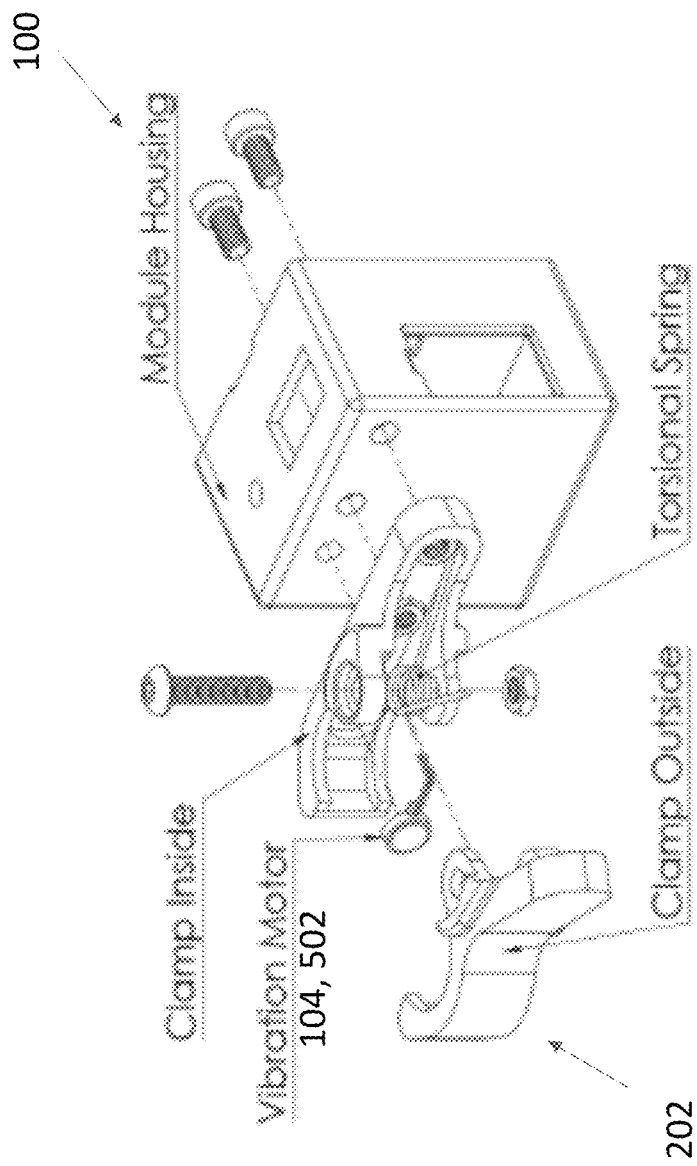
FIG. 5: Clamp Assembly Exploded View
Figure 6:
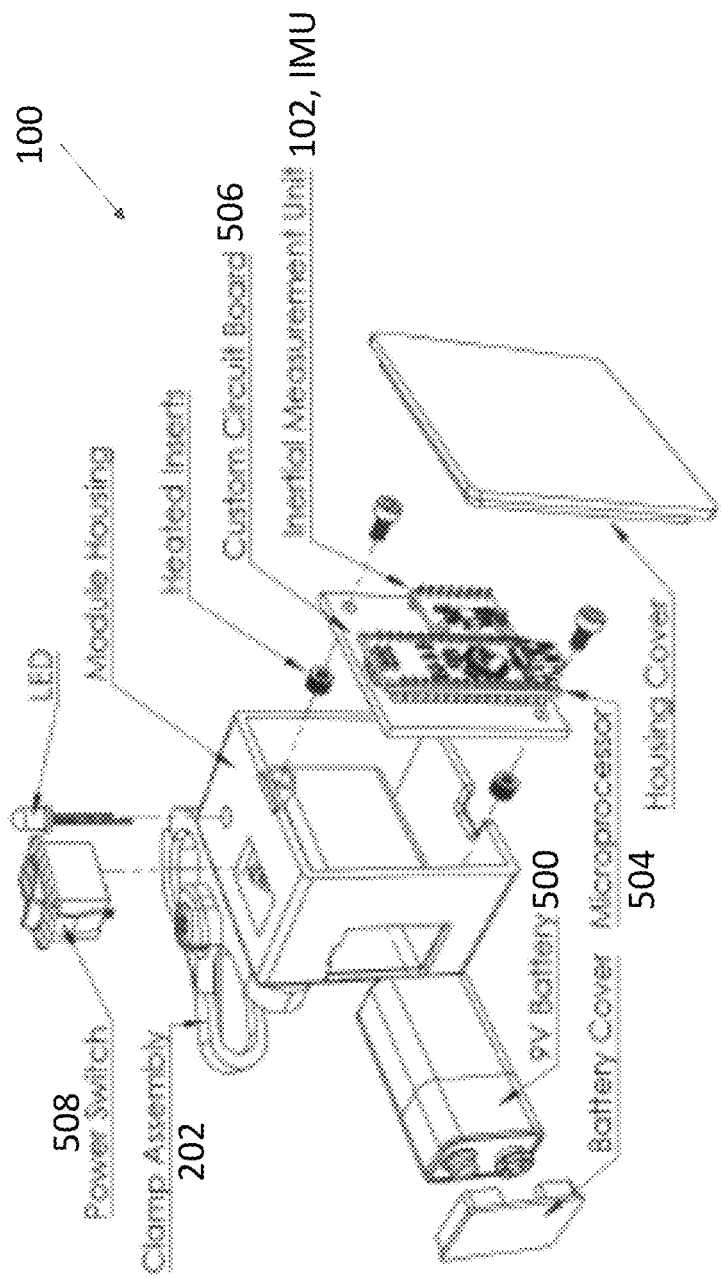
FIG. 6: Electronic Components Exploded View
Figure 7:
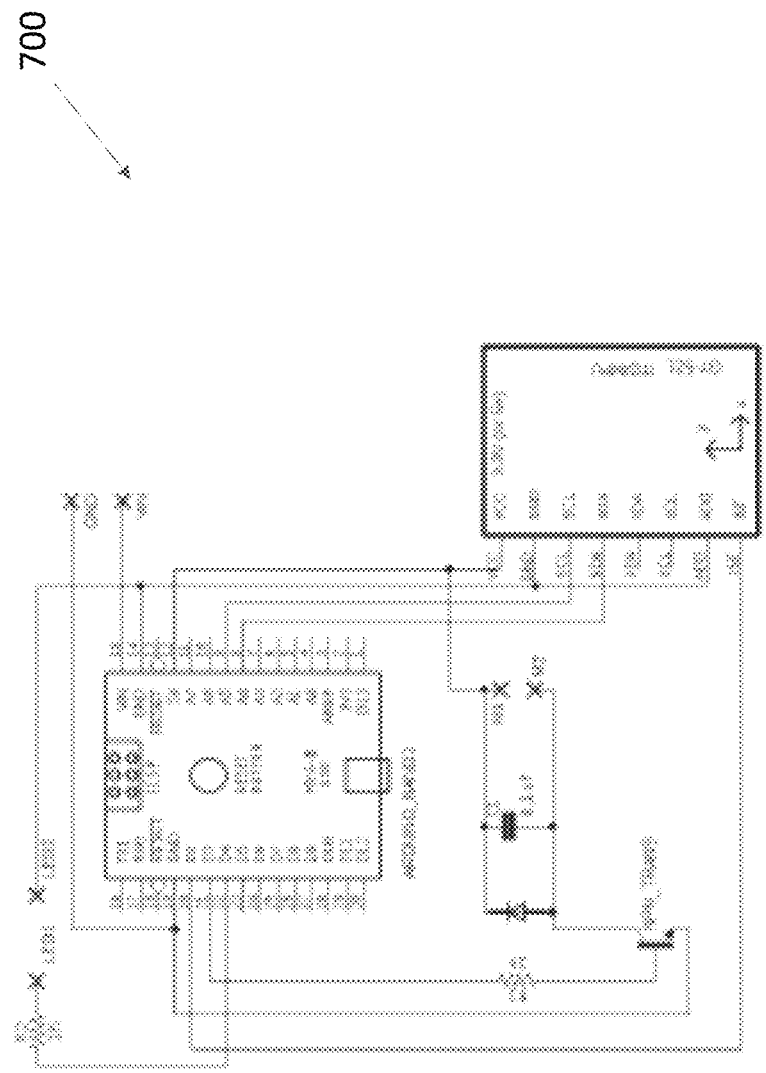
FIG. 7: Schematic of Custom Circuit Board.
Figure 8:
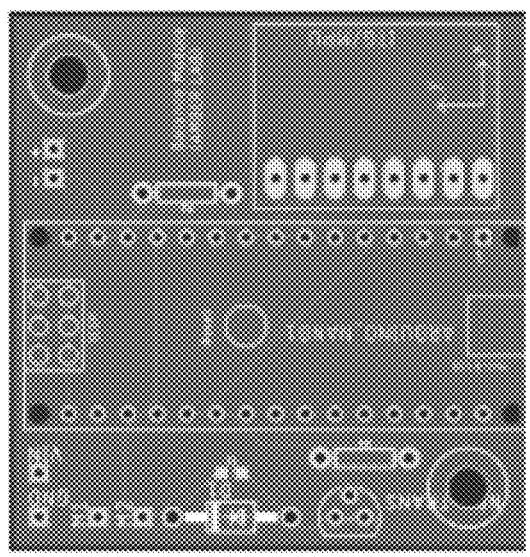
FIG. 8: Image of Custom Circuit Board

In the embodiments shown in FIGS. 5 and 6, the apparatus (e.g., balancing module) comprises a clamp 202, a battery 500, the sensory output device 104 comprising a vibration motor 502, the sensor 102 comprising an Inertial Measurement Unit (IMU), a microprocessor 504, and a custom circuit board 506 that connects the power supply 500 through a power switch 508 to the microprocessor and the microprocessor to the IMU and the vibration motor. An LED is also included to indicate when the module is powered. In addition to the haptic feedback provided by the vibration motor, the LED blinks to provide visual feedback. All of the electronics are housed in the module housing and protected with two covers. The vibration motor is placed on the inside of the clamp so that it is in direct contact with the cane. The module can also be used with flexible straps, shown in FIG. 4, to attach directly to a user. The schematic of the custom circuit board can be seen in FIG. 7. Additionally, the final layout of the printed board can be seen in FIG. 8.

Figure 9:
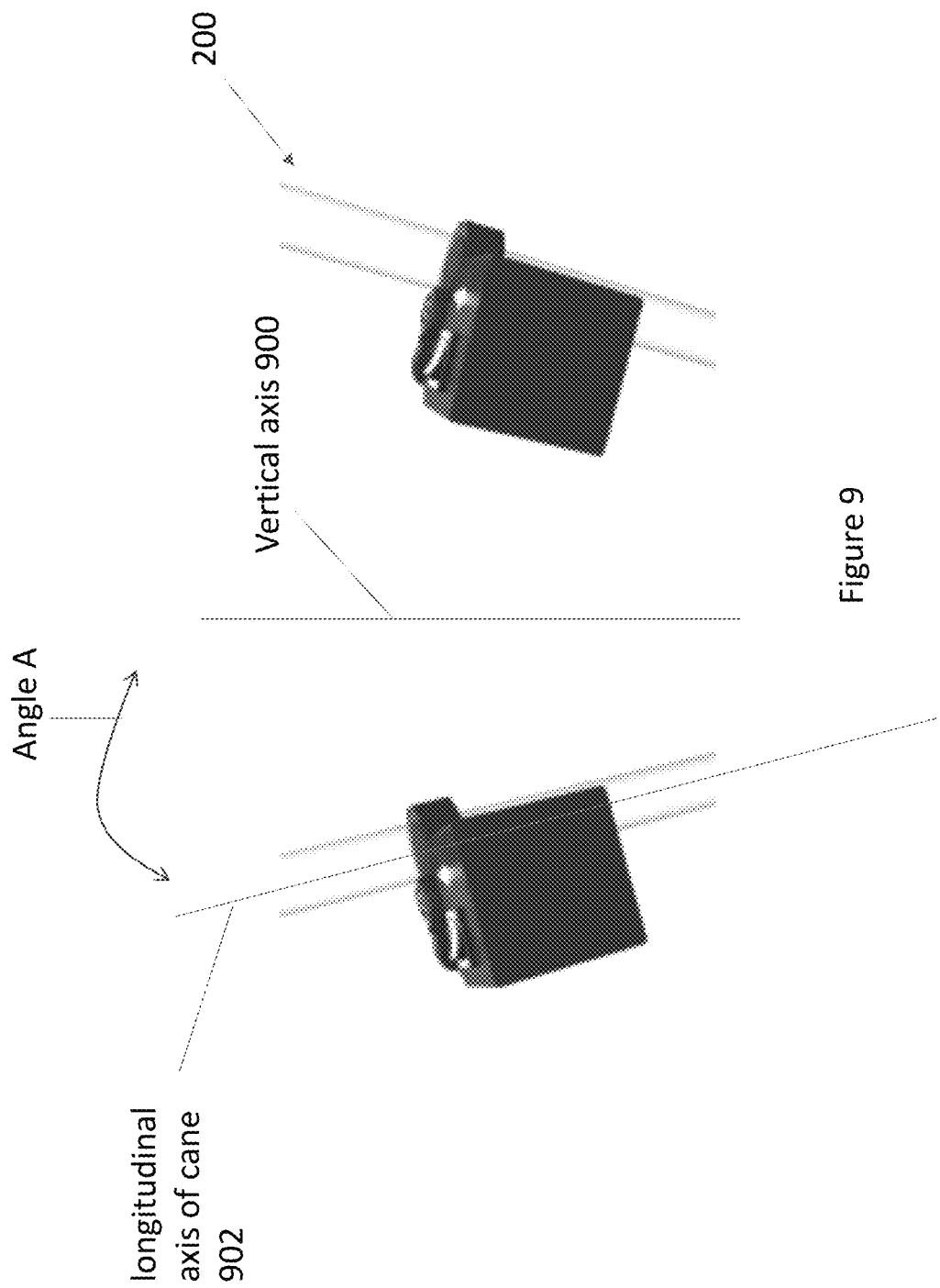
FIG. 9: Configurations that Trigger Haptic Feedback

Different control algorithms can be used to select when the vibration motor activates. In one example, shown in FIG. 9, vibrations occur when the module (or longitudinal axis 902 of the cane attached to the cane) is angled at an angle (e.g., 15 degrees) from a vertical axis 900 in either lateral direction. The vibration motor does not vibrate when the module is angled front or back because these angles occur naturally during the walking gait. The vibration motor does also not vibrate when it is rotated about the central axis of the cane because the cane is rotated when the user turns. However, many different controllers can be used to provide haptic feedback to users about their safety and stability through the use of an BTU and a vibration motor.

II. Exemplary Additional Functionalities

A device according to embodiments described herein include many advanced capabilities. In some examples, the advanced capabilities of the device are tailored to help users with gait training and awareness of body orientation. All variations of the device also utilize hardware that provides real time feedback to the user.

a. Example Vibration Patterns

In various examples, the haptic feedback is provided by vibration patterns selected according to a variety of components such as walking gait data, biomechanics, model of locomotion, and quasi-static stability of human-cane walking. In some examples, vibration patterns are analyzed and compared using advanced techniques including, but not limited to, motion capture.

b. Example Control Algorithms

Figure 10:
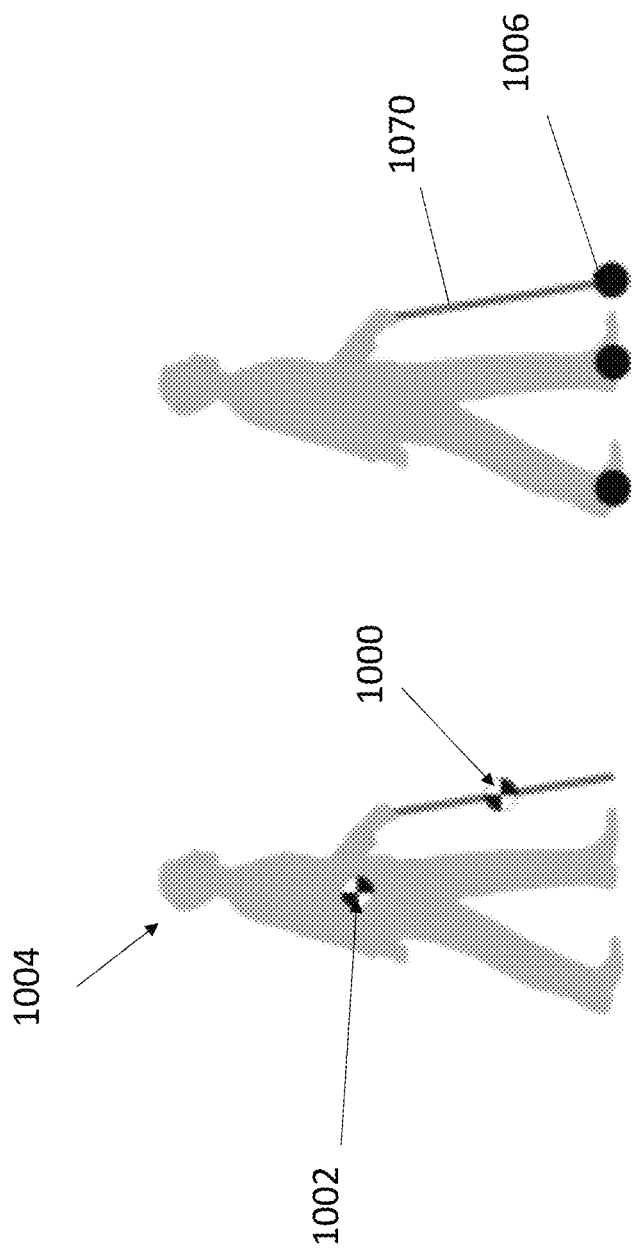
FIG. 10A: Center of Mass Model.
FIG. 10B: Contact Point Model.

In one or more examples, haptic feedback is provided to increase stability of the user. In some examples, stability is defined using the zero-moment point of the user. FIGS. 10A and 10B illustrate two different models in which to view safety of the user. FIG. 10A illustrates the center of mass model using the center of mass 1000 of the walking stick 200 (including device 100) and/or the center of mass 1002 of the user 1004 to define the safety of the human user 1004. FIG. 10B illustrates the contact point model using contact points 1006 to define the safety of the user 1004.

Figure 11:
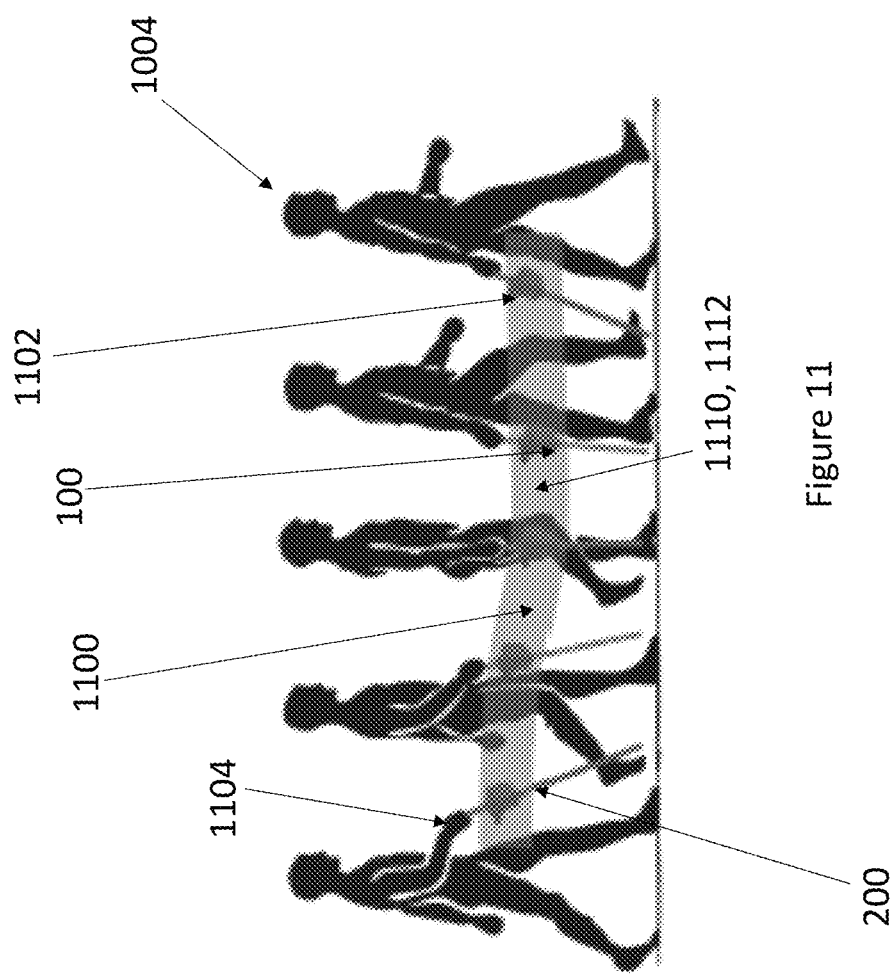
FIG. 11: Example Set of Safe Module Positions

FIG. 11 illustrates an example set 1100 of safe module positions 1102 for the apparatus 100 determined using the control algorithm model when the apparatus 100 is being used to communicate acceptable, safe, and/or stable walking gait. In this example, the apparatus comprises a vibration motor providing haptic feedback (vibration) sensed by the user's 1004 hand 1104. Vibrations outputted from the vibration motor may be transmitted through the cane 200 (e.g., through the handle of the cane) to the hand 1104.

In other examples, more sophisticated control methods or algorithms are used including, but not limited to, a quadratic program (QP) model, a model independent quadratic program (MIQP), a control barrier function, or a control lyapunov function.

In one control barrier function example, a control barrier function is created by defining an enclosed and bounded set of safe module orientations. As the device approaches an unsafe orientation, the control barrier function activates the vibration motor. FIG. 12 illustrates an example set of safe device configurations.

In yet another example, a control barrier function is used with the zero-moment point (ZMP) of the cane-human system. The zero-moment point of the system is calculated using the center of mass 1000, 1002 of each object (center of mass 1000 of cane and center of mass 1002 of the human user 1004) and calculating the location of the entire system where the moment is zero. FIG. 12 illustrates a representation of a set or region 1200 of safe zero-moment points 1202 of a cane-human system. By investigating stable human-cane walking gaits, the area 1200 around the base of a human can be defined as "safe". The control barrier function calculates the ZMP of the system, and activates the vibration motor when the ZMP exists outside of the "safe" area 1200.

c. Connectivity

Other exemplary capabilities added to the device improve its connectivity. Examples include, but are not limited to, wireless communication capabilities, such as Bluetooth, added to facilitate communication with an external platform (such as a mobile application). In one example application, the height of the user and the height of the cane are inputted to the application and the applications uses the height information to calculate a specific zero-moment point based on the angle of the cane. In yet another example, the software program or application changes settings of the device (e.g., the vibration pattern, the maximum vibration amplitude, or the desired maximum allowable angle of deflection) depending on the user input. Other connectivity capabilities include location tracking, allowing users to locate their cane if they were to misplace it.

Additional input to the device adds further refinement, sophistication, and accuracy to the gait training. In some examples, wearable vibration motors provide specific directional haptic feedback to the user. In other examples, wearable sensors (e.g., IMUs) are used to obtain more information about user orientation and user intent. Significantly more complex, refined, accurate, or sophisticated control methods are implemented with more positional information.

d. Power and Hardware

Devices according to examples described herein implement off the shelf or custom microcontrollers. Custom microcontrollers may decrease overall size of the device and maximize the performance of the microprocessor.

In some examples, more advanced battery technology (such as rechargeable lithium ion batteries or smaller coin cell batteries) are incorporated to decrease the overall size of the device.

e. Active Feedback

Figures 13A, 13B:
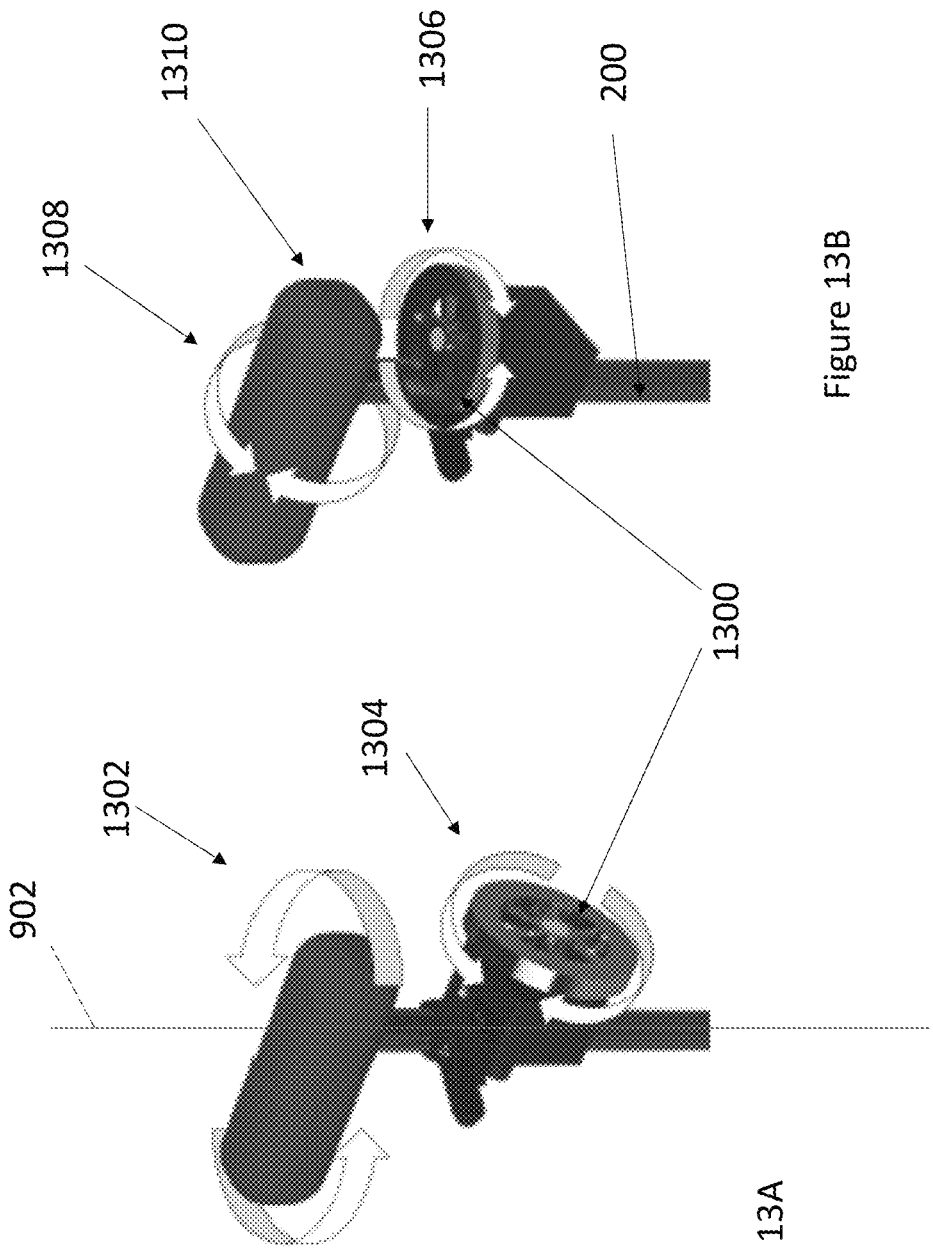

The device is not limited to the use of passive feedback. Active feedback may also be used. For example, addition of a motor provides proprioceptive feedback and active stabilization. For example, the addition of a flywheel to the device provides active stabilization as an additional response to the haptic feedback of the vibration motor. FIG. 13A illustrates an example module 100 with a flywheel 1300 that stabilizes the orientation 1302 of the cane about the central axis of the human user (and/or the longitudinal axis 902 of the cane 200) by providing a rotation 1304 about an axis perpendicular to the central axis or the longitudinal axis 902 of the cane 200. FIG. 13B illustrates an example module 100 with a flywheel 1300, wherein the flywheel provides active stabilization that directly corrects for angle deviations 1308 laterally in the frontal plane by rotating 1306 about an axis parallel to the central axis of the human user or parallel to the longitudinal axis 902 of the cane 200. The frontal plane is the coronal plane or vertical plane that divides the body into ventral (belly) and dorsal (back) sections. Also shown in FIGS. 13A and 13B is the handle 1310 of the cane used to hold the cane and transmit/communicate the haptic feedback (vibrations) to the user's hand.

f. Attachment Methods

A variety of attachment methods are possible. In some examples, the method of attachment is tailored for different types of fall-detection and stabilization. A flexible strap enables the device to be mounted to any part of the body.

In one example, the device strapped to the leg of a user corrects for the amount of knee extension during a gait cycle. Paired with a feature for customizing the angle of vibration, physical therapists can define specific angles of actuation for each of the axes to fit the individual needs of each patient.

FIG. 14 illustrates an example device 100 strapped 400 to the body part 1400a comprising a trunk 1400 (e.g., abdomen) of a human user 1402 to provide haptic feedback tailored for trunk balance. When used in conjunction with physical therapy, the haptic feedback help users become more aware of their posture and whether they are sitting up straight. In one or more examples, the device 100 measures orientation 1404 about an axis perpendicular to the frontal plane and comprises a vibration motor transmitting haptic feedback or vibrations to the trunk so that the user senses the vibrations in the trunk indicating correct or incorrect posture.

Although the additional functionalities are described in the context of haptic feedback, the additional functionalities (e.g., control algorithms) can also be implemented with other types of feedback (e.g., sound, light).

III. Example Applications

Exemplary devices described herein are tailored to prevent falls by providing real-time haptic feedback to the user when they are in an unsafe or unbalanced position. Existing technology is different from our solution because our device is modular and gives immediate real time feedback to the user. In one or more examples, the device delivers haptic feedback through the vibrations of a vibration motor. The module can either be attached to a cane and thus vibrate the cane, or it can be directly attached to the clothing of a user for use without a cane. By providing real-time haptic feedback, the device can be used at home or in a clinical setting to allow patients to practice rehabilitative exercises in a more safe and informative manner. Thus, the device both enhances the user's awareness of their balance and acts as a preventative measure against falls.

Another major use for this device is to assist rehabilitation exercises for stroke patients suffering with impaired balance. Each year, approximately 5 million people worldwide are permanently disabled from stroke as recorded by the World Health Organization. A main component of stroke recovery is regaining a sense of balance. In one or more examples, the device serves as a training tool to provide recovering patients with haptic feedback instructing proper balance techniques. The device has shown to help patients regain a sense of balance through preliminary initial testing performed by physical therapists at Rancho Los Amigos. Since the device serves as both a walking aid and assists with balance training, it may help millions of people regain mobility and reduce their risks of falling.

IV. Process Steps a. Method of Making

Figure 15:
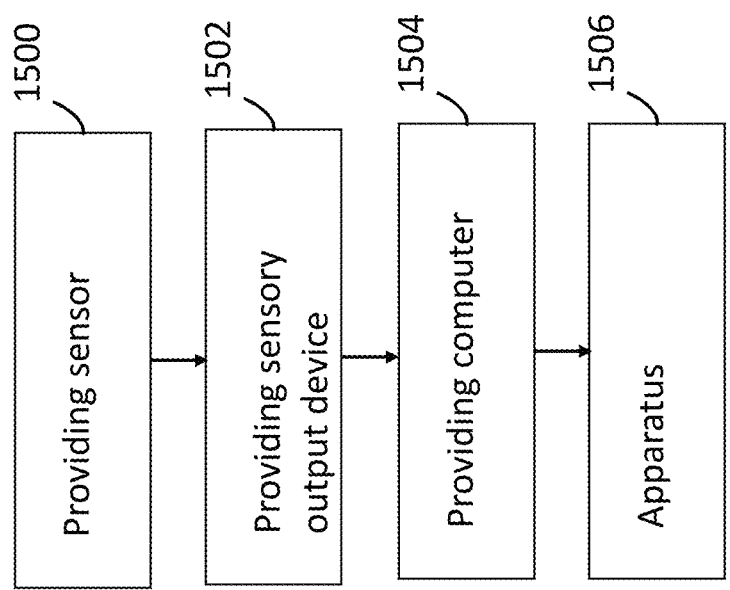
FIG. 15. Method of making an apparatus.

FIG. 15 is a flowchart illustrating a method of making an apparatus useful, for example, as a physical therapy aid, walking aid, or posture corrector.

Block 1500 represents providing a sensor for measuring a measurement of at least one parameter associated with a position of a body part of a user or equipment attached to the user (e.g., human or animal).

Block 1502 represents providing a sensory output device outputting a feedback to the user based on the measurement received from the sensor and in real time with the measuring, the feedback communicates to the user, or transmits a signal to used by user to determine, whether the position is acceptable or unacceptable for maintaining balance, correct posture, or following a predetermined physical therapy exercise.

In one or more examples, the sensory output device comprises a vibration motor (e.g., flatpack vibration motor) or piezoelectric actuator or motor or other haptic output device outputting haptic signals or haptic output that can be sensed by the user. In one or more examples, the haptic device outputs mechanical oscillations ranging in frequency from below 1 Hz up to at least 100 kHz or other frequencies sensed or felt by the human body or hands. In one or more further examples, the sensory output device is a light source (e.g., one or more LEDs) emitting visible light or a sound source (e.g., speaker) emitting sound audible to the user. In one or more examples, the sensory output device outputs the feedback comprising a signal (e.g., vibration, light, or sound) to which the user can instinctively or by reflexively responds with a corrective motion or stopping of the body part. In one or more examples, different signals (e.g., pattern, sequence of pulses) are outputted depending on the desired corrective response. For example, different signals can be interpreted to represent different corrective responses.

Block 1504 represents optionally providing a computer, processor, or microprocessor for performing various functions, including measuring the position or parameter(s) associated with the position from data acquired by the sensor and determining the feedback from the measurement of the position or parameter(s). In various examples, the parameters comprise coordinates in a coordinate system or one or more angles with respect to an axis. Example computers include, but are not limited to, an Arduino™ microcontroller or an ATmega328™ microcontroller.

Block 1506 represents the end result, an apparatus, e.g., as illustrated in FIGS. 1-14. The apparatus is embodied in many ways including, but not limited to, the following.

1. An apparatus 100, comprising:
   a sensor 102 measuring a measurement of at least one parameter associated with a position 1070 of a body part 1400a (e.g., leg, arm, hand trunk, torso) of a user 1004 or equipment 200a (e.g., walking stick or cane 200) attached to, connected to, or held by the user; and
   a sensory output device 104 (e.g., connected to the sensor) outputting a feedback to the user based on the measurement received from the sensor and in real time with the measuring, the feedback communicating to the user whether the position is an acceptable position 1200a or unacceptable position 1200b for maintaining balance, correct posture, or following a predetermined physical therapy or rehabilitation exercise. In one or more examples, the acceptable position 1200a is the position 1070 within a safety region 1200 and the unacceptable position 1200b is outside the safety region 1200.

2. The apparatus of example 1, wherein the feedback is provided to the user within 100 milliseconds of the sensor measuring the measurement.

3. The apparatus of example 1 or 2, wherein the device is a haptic device and the feedback comprises a haptic feedback felt by the user.

4. The apparatus of any of the preceding examples 1-2, wherein the sensor 102 comprises an inertial measurement unit (IMU). Example devices include at least one of a multi axis accelerometer, gyroscope, or other sensors to provide estimation of an object's (e.g., body part's or sensor's 102 or device's 100) orientation in space. Measurements of acceleration, angular rate, and attitude are typical data outputs. In one or more examples, the accelerometer is a 6 axis accelerometer, a 9 axis accelerometer, or an accelerometer having 6 axes or less. Examples include, but are not limited to, an MPU 6050.

5. The apparatus of any of the preceding examples 1-4, wherein the sensory output device 104 comprises a vibration motor 502.

6. The apparatus of any of the preceding examples, further comprising a computer (e.g., processor) 1000 determining whether the at least one parameter is in a predetermined range associated with the acceptable position or the un-acceptable position and the feedback communicates to the user when the at least one parameter is within the predetermined range.

7. The apparatus of example 6, wherein the predetermined range is tailored to the user and comprises data representing acceptable positioning of the body part during the physical therapy exercise customized for the user.

8. The apparatus of example 6, further comprising a computer 1702 inputting the at least one parameter into a model or algorithm determining whether the at least one parameter lies on an acceptable trajectory 1110 commensurate with a predetermined trajectory 1112 for the physical therapy exercise or for maintaining the balance or the posture.

9. The apparatus of example 6, further comprising a computer 1000 inputting the at least one parameter into a model or algorithm determining whether the at least one parameter is associated with the acceptable or unacceptable position.

10. The apparatus of any of the preceding examples 1-9, wherein the position comprises an orientation (e.g. angle A) and the feedback communicates whether the orientation is within or outside an acceptable range so as to guide or train a walking gait of the user.

11. The apparatus of example 10, further comprising a computer determining whether the orientation lies within the acceptable range comprising a predetermined range for stability of the user so as to avoid a fall.

10. The apparatus of example 11, wherein the predetermined range comprises an angle A within 20 degrees of an axis passing through a torso 1400 of the user 1002 or a longitudinal axis 902 of a walking stick or cane 200 attached to the apparatus (e.g., the angle A is 0≤A≤20 degrees with respect to axis 902).

12. The apparatus of example 10 or 11, wherein the stability is defined using a zero-moment point of the user and the computer calculates the zero-point moment of the user in real time using the orientation. 13. A walking stick or cane 200 comprising the apparatus of any of the preceding examples 1-12.

14, The walking stick or cane comprising the apparatus of example 13 and a handle 1310, wherein the sensory output device comprises a vibration motor 502 attached to the handle or cane 200 or stick.

15. The apparatus of any of the examples 1-12, further comprising a strap 400 for attaching the apparatus to the body part comprising a torso 1400.

16. The apparatus of any of the preceding examples 1-15, wherein the feedback communicates the acceptable position so as to provide positive reinforcement to the user.

17. An article of clothing or wearable article comprising the apparatus of any of the preceding examples 1-16.

b. Method of Operating

Figure 16:
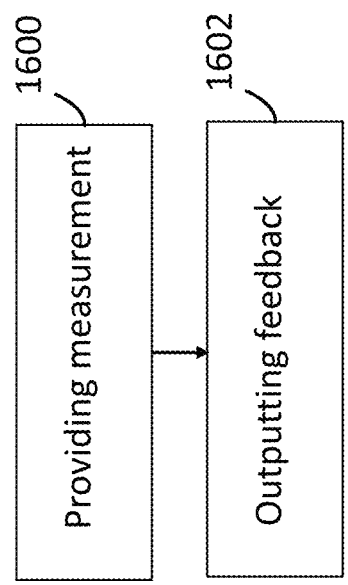
FIG. 16. Method of performing therapy or rehabilitation, or posture or walking assist.

FIG. 16 is a flowchart illustrating a method of providing physical therapy, rehabilitation, training or correcting posture or training or correcting a walking gait.

Block 1600 represents providing a measurement at least one parameter associated with a position of a body part of a user or an equipment attached to the user.

Block 1602 represents outputting a feedback to the user based on the measurement received from the sensor and in real time with the measuring, the feedback communicating to the user whether the position is acceptable or unacceptable for maintaining balance, correct posture, or following a predetermined physical therapy exercise.

The method can be implemented in a variety of ways including, but not limited to, the following.

1. The method further comprising determining whether the at least one parameter is in a predetermined range associated with the acceptable position or the un-acceptable position and wherein the feedback communicates to the user when the at least one parameter is within the predetermined range.

2. The method of example 1 further comprising tailoring the predetermined range to the user so that the predetermined range comprises data representing acceptable positioning of the body part during the physical therapy exercise customized for the user.

3. The method of any of the preceding examples wherein the feedback is communicated only when the position is a correct position.

3. The method of examples 1 or 2, wherein the position comprises an orientation.

4. The method implemented using the apparatus of any of the examples 1-17 above.

V. Hardware Environment

Figure 17:
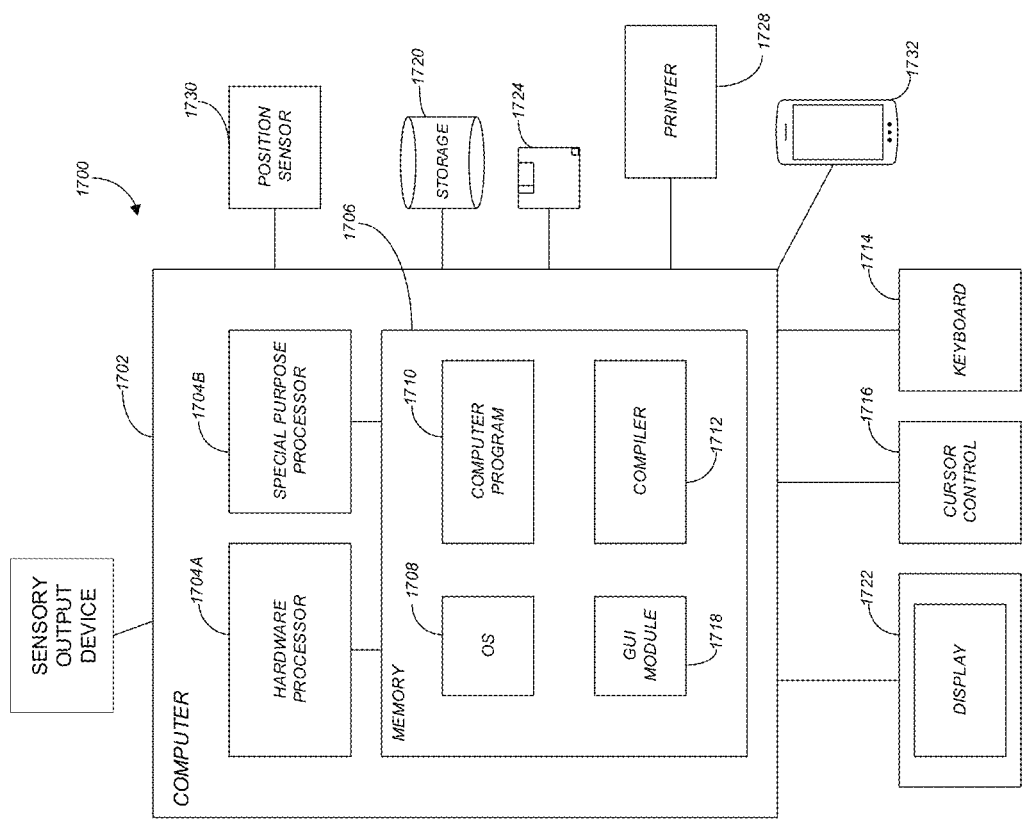
FIG. 17. Example hardware environment.

FIG. 17 is an exemplary hardware and software environment 1700 (referred to as a computer-implemented system and/or computer-implemented method) used to implement one or more embodiments of the invention. The hardware and software environment includes a computer 1702 and may include peripherals. Computer 1702 may be a user/client computer, server computer, or may be a database computer. The computer 1702 comprises a hardware processor 1704A and/or a special purpose hardware processor 1704B (hereinafter alternatively collectively referred to as processor 1704) and a memory 1706, such as random access memory (RAM). The computer 1702 may be coupled to, and/or integrated with, other devices, including input/output (I/O) devices such as a keyboard 1714, a cursor control device 1716 (e.g., a mouse, a pointing device, pen and tablet, touch screen, multi-touch device, etc.) and a printer 1728. In one or more embodiments, computer 1702 may be coupled to, or may comprise, a portable or media viewing/listening device 1732 (e.g., an MP3 player, IPOD, NOOK, portable digital video player, cellular device, personal digital assistant, etc.). In yet another embodiment, the computer 1702 may comprise a multi-touch device, mobile phone, gaming system, internet enabled television, television set top box, or other internet enabled device executing on various platforms and operating systems.

In one embodiment, the computer 1702 operates by the hardware processor 1704A performing instructions defined by the computer program 1710 (e.g., a computer-aided design [CAD] application) under control of an operating system 1708. The computer program 1710 and/or the operating system 1708 may be stored in the memory 1706 and may interface with the user and/or other devices to accept input and commands and, based on such input and commands and the instructions defined by the computer program 1710 and operating system 1708, to provide output and results.

Output/results may be presented on the display 1722 or provided to another device for presentation or further processing or action. In one embodiment, the display 1722 comprises a liquid crystal display (LCD) having a plurality of separately addressable liquid crystals. Alternatively, the display 1722 may comprise a light emitting diode (LED) display having clusters of red, green and blue diodes driven together to form full-color pixels. Each liquid crystal or pixel of the display 1722 changes to an opaque or translucent state to form a part of the image on the display in response to the data or information generated by the processor 1704 from the application of the instructions of the computer program 1710 and/or operating system 1708 to the input and commands. The image may be provided through a graphical user interface (GUI) module 1718. Although the GUI module 1718 is depicted as a separate module, the instructions performing the GUI functions can be resident or distributed in the operating system 1708, the computer program 1710, or implemented with special purpose memory and processors.

In one or more embodiments, the display 1722 is integrated with/into the computer 1702 and comprises a multi-touch device having a touch sensing surface (e.g., track pod or touch screen) with the ability to recognize the presence of two or more points of contact with the surface. Examples of multi-touch devices include mobile devices (e.g., IPHONE, NEXUS S, DROID devices, etc.), tablet computers (e.g., IPAD, HP TOUCHPAD, SURFACE Devices, etc.), portable/handheld game/music/video player/console devices (e.g., IPOD TOUCH, MP3 players, NINTENDO SWITCH, PLAYSTATION PORTABLE, etc.), touch tables, and walls (e.g., where an image is projected through acrylic and/or glass, and the image is then backlit with LEDs).

Some or all of the operations performed by the computer 1702 according to the computer program 1710 instructions may be implemented in a special purpose processor 1704B. In this embodiment, some or all of the computer program 1710 instructions may be implemented via firmware instructions stored in a read only memory (ROM), a programmable read only memory (PROM) or flash memory within the special purpose processor 1704B or in memory 1706. The special purpose processor 1704B may also be hardwired through circuit design to perform some or all of the operations to implement the present invention. Further, the special purpose processor 1704B may be a hybrid processor, which includes dedicated circuitry for performing a subset of functions, and other circuits for performing more general functions such as responding to computer program 1710 instructions. In one embodiment, the special purpose processor 1704B is an application specific integrated circuit (ASIC) or field programmable gate array (FPGA).

The computer 1702 may also implement a compiler 1712 that allows an application or computer program 1710 written in a programming language such as C, C++, Assembly, SQL, PYTHON, PROLOG, MATLAB, RUBY, RAILS, HASKELL, or other language to be translated into processor 1704 readable code. Alternatively, the compiler 1712 may be an interpreter that executes instructions/source code directly, translates source code into an intermediate representation that is executed, or that executes stored precompiled code. Such source code may be written in a variety of programming languages such as JAVA, JAVASCRIPT, PERL, BASIC, etc. After completion, the application or computer program 1710 accesses and manipulates data accepted from I/O devices and stored in the memory 1706 of the computer 1702 using the relationships and logic that were generated using the compiler 1712.

The computer 1702 also optionally comprises an external communication device such as a modem, satellite link, Ethernet card, or other device for accepting input from, and providing output to, other computers 1702.

In one embodiment, instructions implementing the operating system 1708, the computer program 1710, and the compiler 1712 are tangibly embodied in a non-transitory computer-readable medium, e.g., data storage device 1720, which could include one or more fixed or removable data storage devices, such as a zip drive, floppy disc drive 1724, hard drive, CD-ROM drive, tape drive, etc. Further, the operating system 1708 and the computer program 1710 are comprised of computer program 1710 instructions which, when accessed, read and executed by the computer 1702, cause the computer 1702 to perform the steps necessary to implement and/or use the present invention or to load the program of instructions into a memory 1706, thus creating a special purpose data structure causing the computer 1702 to operate as a specially programmed computer executing the method steps described herein. Computer program 1710 and/or operating instructions may also be tangibly embodied in memory 1706 and/or data communications devices 1730, thereby making a computer program product or article of manufacture according to the invention. As such, the terms "article of manufacture," "program storage device," and "computer program product," as used herein, are intended to encompass a computer program accessible from any computer readable device or media.

Of course, those skilled in the art will recognize that any combination of the above components, or any number of different components, peripherals, and other devices, may be used with the computer 1702.

FIG. 18 schematically illustrates a typical distributed/cloud-based computer system 1800 using a network 1804 to connect client computers 1802 to server computers 1806. A typical combination of resources may include a network 1804 comprising the Internet, LANs (local area networks), WANs (wide area networks), SNA (systems network architecture) networks, or the like, clients 1802 that are personal computers or workstations (as set forth in FIG. 17), and servers 1806 that are personal computers, workstations, minicomputers, or mainframes (as set forth in FIG. 17). However, it may be noted that different networks such as a cellular network (e.g., GSM [global system for mobile communications] or otherwise), a satellite based network, or any other type of network may be used to connect clients 1802 and servers 1806 in accordance with embodiments of the invention.

A network 1804 such as the Internet connects clients 1802 to server computers 1806. Network 1804 may utilize ethernet, coaxial cable, wireless communications, radio frequency (RF), etc. to connect and provide the communication between clients 1802 and servers 1806. Further, in a cloud-based computing system, resources (e.g., storage, processors, applications, memory, infrastructure, etc.) in clients 1802 and server computers 1806 may be shared by clients 1802, server computers 1806, and users across one or more networks. Resources may be shared by multiple users and can be dynamically reallocated per demand. In this regard, cloud computing may be referred to as a model for enabling access to a shared pool of configurable computing resources.

Clients 1802 may execute a client application or web browser and communicate with server computers 1806 executing web servers 1810. Such a web browser is typically a program such as MICROSOFT INTERNET EXPLORER/ EDGE, MOZILLA FIREFOX, OPERA, APPLE SAFARI, GOOGLE CHROME, etc. Further, the software executing on clients 1802 may be downloaded from server computer 1806 to client computers 1802 and installed as a plug-in or ACTIVEX control of a web browser. Accordingly, clients 1802 may utilize ACTIVEX components/component object model (COM) or distributed COM (DCOM) components to provide a user interface on a display of client 1802. The web server 1810 is typically a program such as MICROSOFT'S INTERNET INFORMATION SERVER.

Web server 1810 may host an Active Server Page (ASP) or Internet Server Application Programming Interface (ISAPI) application 1812, which may be executing scripts. The scripts invoke objects that execute business logic (referred to as business objects). The business objects then manipulate data in database 1816 through a database management system (DBMS) 1814. Alternatively, database 1816 may be part of, or connected directly to, client 1802 instead of communicating/obtaining the information from database 1816 across network 1804. When a developer encapsulates the business functionality into objects, the system may be referred to as a component object model (COM) system.

Accordingly, the scripts executing on web server 1810 (and/or application 1812) invoke COM objects that implement the business logic. Further, server 1806 may utilize MICROSOFT'S TRANSACTION SERVER (MTS) to access required data stored in database 1816 via an interface such as ADO (Active Data Objects), OLE DB (Object Linking and Embedding DataBase), or ODBC (Open DataBase Connectivity).

Generally, these components 1800-1816 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/ or data, when read, executed, and/or interpreted, results in the steps necessary to implement and/or use the present invention being performed.

Although the terms "user computer", "client computer", and/or "server computer" are referred to herein, it is understood that such computers 1802 and 1806 may be interchangeable and may further include thin client devices with limited or full processing capabilities, portable devices such as cell phones, notebook computers, pocket computers, multi-touch devices, and/or any other devices with suitable processing, communication, and input/output capability.

Of course, those skilled in the art will recognize that any combination of the above components, or any number of different components, peripherals, and other devices, may be used with computers 1802 and 1806. Embodiments of the invention are implemented as a software/CAD application on a client 1802 or server computer 1806. Further, as described above, the client 1802 or server computer 1806 may comprise a thin client device or a portable device that has a multi-touch-based display. In one or more examples, the sensor measuring the parameters associated with position and/or the sensory output device include the computer system, or the computer system is connected to at least one of the sensory output device and the sensor measuring the position.

VI. References

The following references are incorporated by reference herein.

[1] E. R. Burns, J. A. Stevens, and R. Lee, "The direct costs of fatal and non-fatal falls among older adults—United States," *Journal of Safety Research*, 2016.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An apparatus, comprising:
   a sensor measuring a measurement of at least one parameter associated with a position of a body part of a user or equipment attached to the user; and
   a sensory output device outputting a feedback to the user based on the measurement received from the sensor and in real time with the measuring, the feedback communicating to the user whether the position is acceptable or unacceptable for maintaining balance, correct posture, or following a predetermined physical therapy exercise, wherein the position comprises an orientation and the feedback communicates whether the orientation is within or outside an acceptable range so as to guide a walking gait of the user or avoid a fall; and
   a computer determining whether the orientation lies within the acceptable range for stability of the user so as to avoid the fall or to guide the walking gait, wherein the acceptable range comprises an angle within 20 degrees of an axis passing through the body part comprising a torso of the user or a longitudinal axis of the equipment comprising a walking stick or cane attached to the apparatus.

2. The apparatus of claim 1, wherein the feedback is provided to the user within 100 milliseconds of the sensor measuring the measurement.

3. The apparatus of claim 1, wherein the device is a haptic device and the feedback comprises a haptic feedback felt by the user.

4. The apparatus of claim 1, wherein the sensor comprises an inertial measurement unit.

5. The apparatus of claim 4, wherein the sensory output device comprises a vibration motor.

6. The apparatus of claim 1, further comprising the computer determining whether the at least one parameter is in a predetermined range associated with the acceptable range or the un-acceptable range.

7. The apparatus of claim 6, wherein the predetermined range is tailored to the user and comprises data representing acceptable positioning of the body part during the physical therapy exercise customized for the user.

8. The apparatus of claim 6, further comprising the computer inputting the at least one parameter into a model or algorithm determining whether the at least one parameter lies on an acceptable trajectory commensurate with a predetermined trajectory for the physical therapy exercise or for maintaining the balance or the posture.

9. The apparatus of claim 6, further comprising the computer inputting the at least one parameter into a model or algorithm determining whether the at least one parameter is associated with the acceptable or unacceptable position.

10. The apparatus of claim 1, wherein the stability is defined using a zero-moment point of the user and the computer calculates the zero-moment point of the user in real time using the orientation.

11. The walking stick or the cane comprising the apparatus of claim 1.

12. The walking stick or cane comprising the apparatus of claim 11 and a handle, wherein the sensory output device comprises a vibration motor attached to the handle.

13. The apparatus of claim 1, further comprising a strap for attaching the apparatus to the body part comprising the torso.

14. The apparatus of claim 1, wherein the feedback communicates the position that is acceptable so as to provide positive reinforcement to the user.

15. An article of clothing or wearable article comprising the apparatus of claim 1.

16. A method of providing physical therapy, correcting posture or correcting a walking gait, comprising:
providing a measurement at least one parameter associated with a position of a body part of a user or an equipment attached to the user; and
outputting a feedback to the user based on the measurement received from the sensor and in real time with the measuring, the feedback communicating to the user whether the position is acceptable or unacceptable for maintaining balance, correct posture, or following a predetermined physical therapy exercise, wherein:
the position comprises an orientation and the feedback communicates whether the orientation is within or outside an acceptable range so as to guide a walking gait of the user or avoid a fall of the user; and
the orientation lies within the acceptable range for stability of the user so as to avoid the fall or guide the walking gait of the user, wherein the acceptable range comprises an angle within 20 degrees of an axis passing through the body part comprising a torso of the user or a longitudinal axis of the apparatus comprising a walking stick or cane.

17. The method of claim 16, further comprising tailoring the acceptable range to the user so that the acceptable range comprises data representing acceptable positioning of the body part during the physical therapy exercise customized for the user.

18. The method of claim 16, further comprising providing the feedback using a sensory output device comprising a vibration motor attached to a handle of the walking stick or the cane.

* * * * *